US008903513B2

(12) United States Patent
Ollivier

(10) Patent No.: US 8,903,513 B2
(45) Date of Patent: *Dec. 2, 2014

(54) APPARATUS AND SYSTEM FOR IMPLANTING AN AUTONOMOUS INTRACARDIAC CAPSULE

(71) Applicant: Sorin CRM S.A.S., Clamart Cedex (FR)

(72) Inventor: Jean-François Ollivier, Villiers-le-Bacle (FR)

(73) Assignee: Sorin CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/041,627

(22) Filed: Sep. 30, 2013

(65) Prior Publication Data

US 2014/0031836 A1  Jan. 30, 2014

Related U.S. Application Data

(63) Continuation of application No. 13/160,407, filed on Jun. 14, 2011, now Pat. No. 8,548,605.

(30) Foreign Application Priority Data

Jun. 14, 2010  (FR) ..................................... 10 54699

(51) Int. Cl.
*A61N 1/05* (2006.01)
*A61N 1/375* (2006.01)
(52) U.S. Cl.
CPC .............. *A61N 1/059* (2013.01); *A61N 1/3756* (2013.01); *A61N 1/0587* (2013.01); *A61N 1/0573* (2013.01); *A61N 1/375* (2013.01)
USPC ....................................................... 607/127

(58) Field of Classification Search
USPC .......................... 600/375; 607/126–128, 131
See application file for complete search history.

(56) References Cited

U.S. PATENT DOCUMENTS

| 4,256,115 A | 3/1981 | Bilitch |
| 4,957,118 A | 9/1990 | Erlebacher |
| 5,425,755 A | 6/1995 | Doan |

(Continued)

FOREIGN PATENT DOCUMENTS

| EP | 0 568 463 | 11/1993 |
| EP | 0 602 859 | 6/1994 |

(Continued)

OTHER PUBLICATIONS

Preliminary Search Report for French Patent Application No. 1054699, dated Feb. 4, 2011, 2 pages.

*Primary Examiner* — Luther Behringer
(74) *Attorney, Agent, or Firm* — Foley & Lardner LLP

(57) ABSTRACT

A system and method for implantation of an autonomous intracardiac capsule. The autonomous capsule includes a cylindrical body with an anchoring screw for penetrating a tissue wall, and at least one coupling finger radially projecting outwards. An implantation accessory includes a lead body and a helical guide, for guiding and driving by rotation the capsule. This helical guide is integral with the lead body, and its inner diameter is sufficient to contain that cylindrical body of the capsule therein. The helix direction of the helical guide is opposite to that of the anchoring screw such that continued rotational motion imparted on the lead body drives the anchoring screw into the target tissue and then emerges the capsule from the helical guide. The helical guide is resiliently compressible in axial direction, and its helix pitch is increased in the free distal end portion.

23 Claims, 3 Drawing Sheets

(56) References Cited

U.S. PATENT DOCUMENTS

| | | | |
|---|---|---|---|
| 5,466,255 | A | 11/1995 | Franchi |
| 6,141,588 | A | 10/2000 | Cox et al. |
| 6,409,674 | B1 | 6/2002 | Brockway et al. |
| 7,162,310 | B2 | 1/2007 | Doan |
| 8,010,209 | B2 | 8/2011 | Jacobson |
| 2006/0136004 | A1 | 6/2006 | Cowan et al. |
| 2007/0047681 | A1 | 3/2007 | Chan et al. |
| 2007/0088397 | A1 | 4/2007 | Jacobson |
| 2007/0088405 | A1 | 4/2007 | Jacobson |
| 2007/0135882 | A1 | 6/2007 | Drasler et al. |
| 2009/0082827 | A1 | 3/2009 | Kveen et al. |
| 2009/0082828 | A1 | 3/2009 | Ostroff |
| 2009/0204170 | A1 | 8/2009 | Hastings et al. |

FOREIGN PATENT DOCUMENTS

| | | |
|---|---|---|
| WO | WO-2007/047681 | 4/2007 |
| WO | WO-2007/067231 | 6/2007 |
| WO | WO-2009/039400 | 3/2009 |

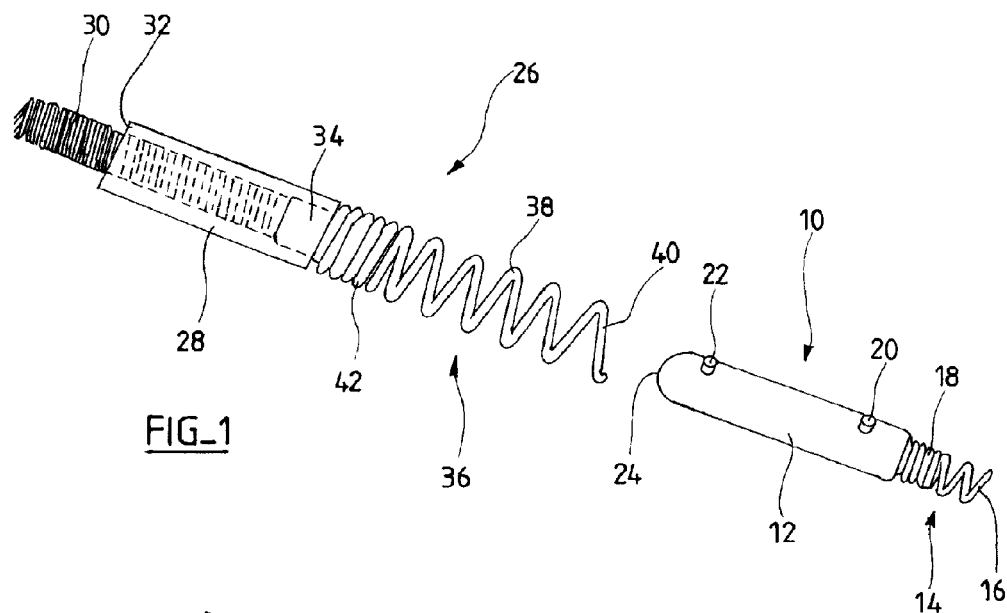
FIG_1
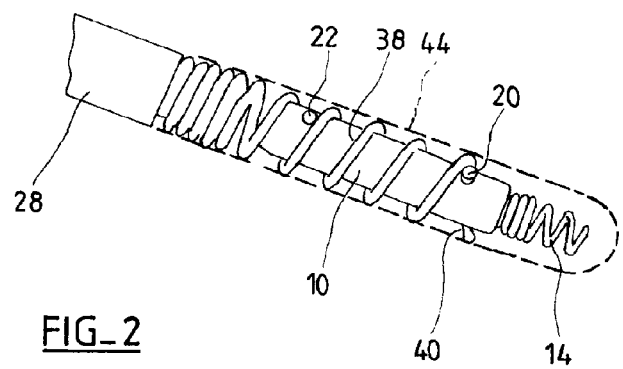
FIG_2
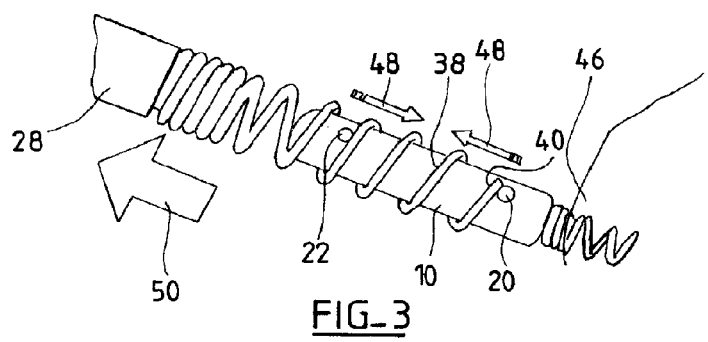
FIG_3

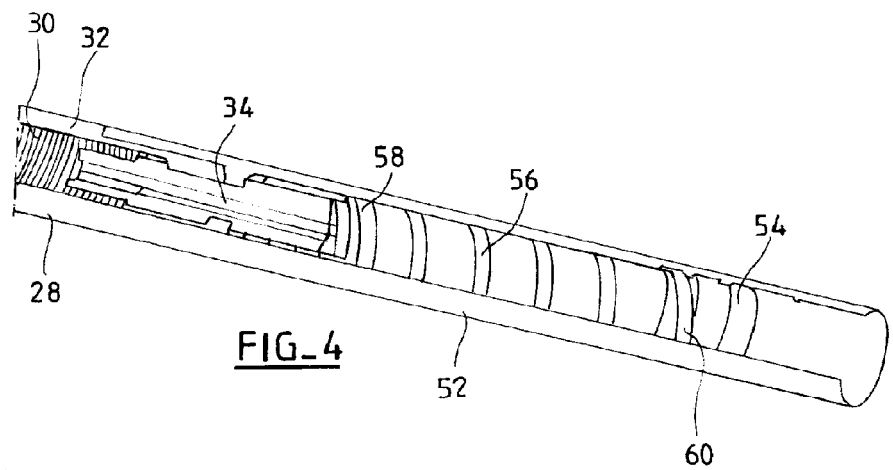
FIG_4
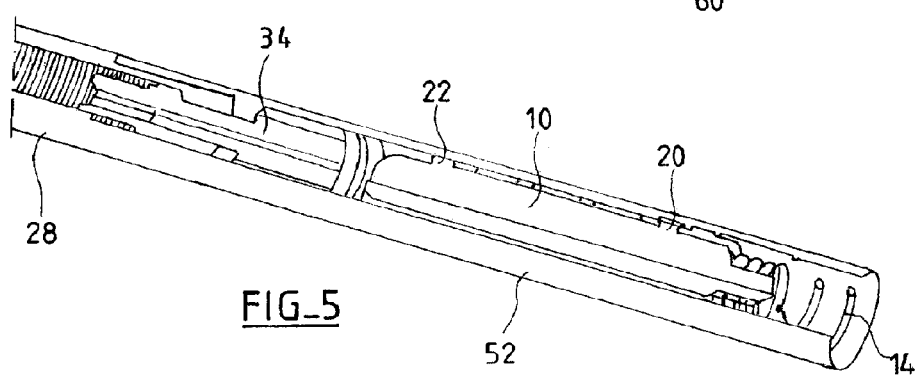
FIG_5
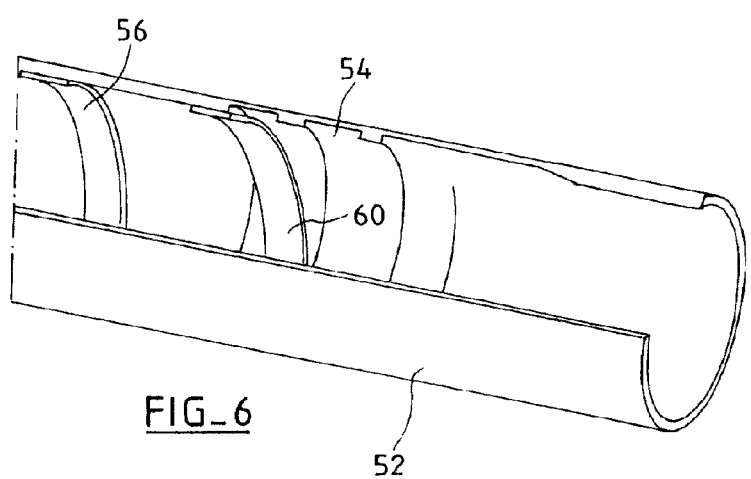
FIG_6

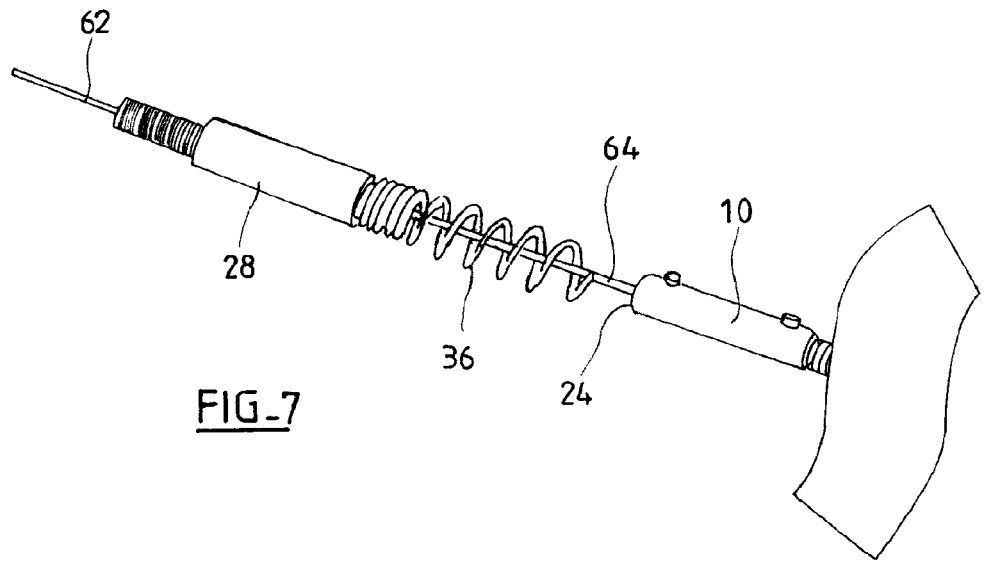
FIG_7
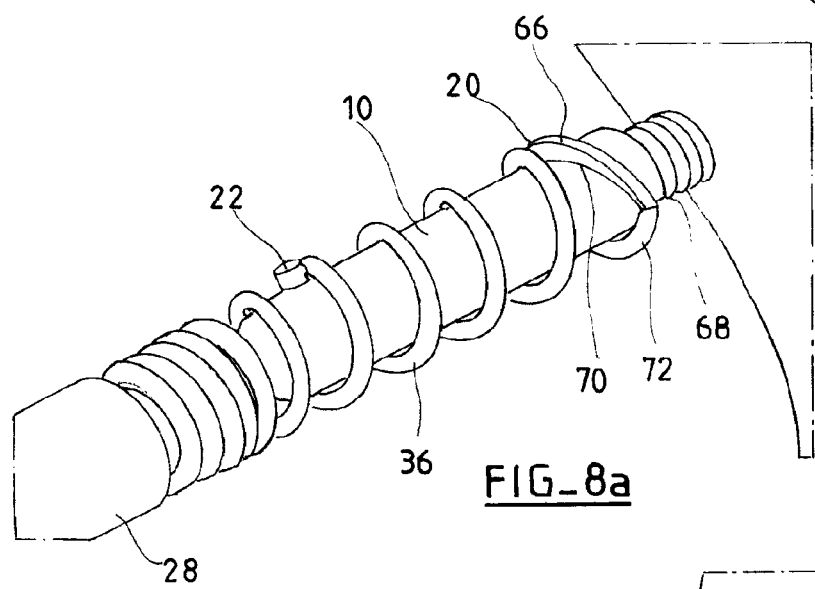
FIG_8a
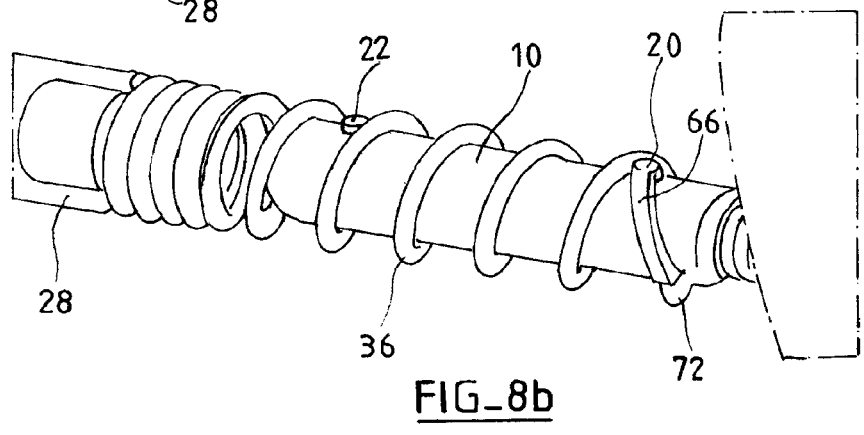
FIG_8b

APPARATUS AND SYSTEM FOR IMPLANTING AN AUTONOMOUS INTRACARDIAC CAPSULE

RELATED APPLICATION

The present application is a continuation of U.S. patent application Ser. No. 13/160,407 filed Jun. 14, 2011, now issued as U.S. Pat. No. 8,548,605, which claims the benefit of French Application No. 10/54699 entitled "Autonomous Intracardiac Capsule And Its Implantation Accessory" and filed Jun. 14, 2010, both of which are hereby incorporated by reference in their entireties.

FIELD OF THE INVENTION

The present invention relates to "active implantable medical devices" as defined by the 20 Jun. 1990 Directive 90/385/EEC of the Council of the European Communities, particularly to devices that continuously monitor a patient's heart rhythm and deliver to the heart, if necessary, electrical stimulation, resynchronization, cardioversion and/or defibrillation pulses in response to a rhythm disorder detected by the device, and even more particularly to the implantation of autonomous capsules that are implanted in a heart chamber with no physical, wired connection to a remote device, for remote monitoring of the patient.

BACKGROUND

Autonomous capsules, also referred to as "leadless capsules," including without limitation autonomous intracardiac capsules (collectively hereinafter referred to as a "capsule"), are distinguished from wired electrodes and sensors that are placed at the distal end of a lead, and connected by a conductor traversing the length of the lead to a device connected at the opposite (proximal) end of the lead. Such capsules are, for example, described in US Patent Publication No. 2007/0088397 A1 and PCT Publication WO 2007/047681 A2 (Nanostim, Inc.) and US Patent Publication No. 2006/0136004 A1 (EBR Systems, Inc.).

These capsules are usually cylindrical structures having a long axis and a diameter. They are usually attached directly to the heart tissue by a projecting helical anchoring screw. The anchoring screw axially extends from the cylindrical body of the capsule and is designed to penetrate the heart tissue by screwing into the implant site.

Of course, to enable data exchange with a remote device, such capsules incorporate a transmitter/receiver for wireless communication with the remote device. A remote device in this context may be an active implantable medal device (e.g., a housing of stimulation pulse generator) or an external device such as a programmer or other device for monitoring a patient.

The capsule can also incorporate a sensor to locally measure the value of a parameter such as, for example, the oxygen level in the blood and/or the acceleration of the heart wall. These capsules can also be detection/stimulation capsules with means to collect depolarization potentials of the myocardium and/or deliver pacing pulses to the site where the capsule is implanted. Such a detection/stimulation capsule then includes an appropriate electrode, which can be, for example, an active portion of the anchoring screw.

In general, the capsule may be an epicardial capsule, attached to the outer wall of the heart, or an endocardial capsule, attached to the inner wall of a ventricular or an atrial cavity. However, It should be understood that the present invention is not limited to a particular type of capsule, and it applies equally to any type of capsule, regardless of its functional purpose.

In the case of an endocardial capsule, the difficulty of implantation is increased because the implantation path involves going through the peripheral venous system. With the assistance of fluoroscopy, the capsule may be directed to a selected implant site, a known method that is both precise and perfectly secure. Once the implant site is reached and the capsule is anchored in the wall, the operator may then operate the "release" of the capsule, and disconnect it from an associated implantation accessory.

US Patent Publication No. 2009/0204170 A1 (Cardiac Pacemakers, Inc.) describes a capsule for electrical stimulation and an accessory tool for its implantation, in which the capsule is guided by a catheter to the implant site within a directing tube pressed against the heart wall, and then progressively screwed into the heart wall by a driving stylet extending into the lumen of the catheter.

The general acceptance by persons of ordinary skill in the art of the use of endocardial capsules relies on an ability to provide a delivery system that is capable of securing the implantation of these capsules, according to the following:

An implantation procedure similar to current practice, allowing practitioners to make use of well-known and well-controlled lead manipulation gestures: e.g., subclavian puncture, insertion and manipulation of a catheter through preformed stylets during an approach to the selected implantation site, fixation with screws or tines, etc.;

Standard Environment in the Operating Room;

Limiting the risk of "carotage" of tissue due to an excessive tightening that may damage or, even worse, puncture the wall (especially in the case of implantation in a thin wall such as the atrial septum);

Possibility of postoperatively withdrawing and/or repositioning the capsule in case of problems, even after a release of the capsule from its delivery system;

Limiting the consequences of a capsule migration in case of displacement during the acute phase of an intervention; and Certainty of a good anchoring of the capsule before removing the implantation accessory.

OBJECT AND SUMMARY

The present invention is directed to a system comprising a capsule and an in situ implantation accessory, a combination in itself known, particularly from the US Published Patent Application 2009/0204170 A1, and improvements thereto. In accordance with the present invention, the capsule preferably comprises a tubular cylindrical body having at one end a projecting helical anchoring screw axially extending from the cylindrical body and, at least one coupling finger secured to the cylindrical body that extends radially outward. The helical anchoring screw is configured to penetrate into the tissue of the wall of a cavity, ventricle or atrium, of the heart. The implantation accessory has at its distal end a disconnectable means for supporting and guiding the capsule to the implantation site, and for rotational driving of the capsule to allow simultaneous driving of the anchoring screw and screwing it into the wall of the heart cavity.

In accordance with a preferred embodiment, the implantation accessory includes a lead body with a sheath of deformable material having at its distal end a helical guide forming said disconnectable means for supporting, guiding, and rotating the capsule. The helical guide extends axially from the lead body and is attached to the latter in rotation and in translation. The inside diameter of the helical guide is homologous to the outside diameter of the cylindrical body of the capsule so as to house the latter inside, with the at least one coupling finger protruding between the coils of the helical guide. The helix direction of the helical guide is opposite to that of the anchoring screw.

In a first embodiment, the helical guide is a projecting helix axially extending from the distal end of the lead body, including a resiliently compressible helix in the axial direction and whose helix pitch is increased in its free distal end portion.

Preferably, the capsule comprises two coupling fingers, one located towards the distal end of the capsule and the other located towards the proximal end of the capsule. The spacing between the two coupling fingers along the axial direction of the capsule is selected to provide a compression of the helix when the cylindrical body of the capsule is completely housed inside the helical guide. Advantageously, when the cylindrical body of the capsule is completely housed inside the helical guide, this assembly also includes a protective soluble coating covering the capsule equipped with its anchoring screw within the helical guide. More preferably, the capsule includes a reset ramp extending from the coupling finger located at the distal end. The reset ramp forms a portion of a helical thread with a helix direction opposite to that of helical guide, and is able to contact at its proximal end and engage with free end of the helical guide.

In a second embodiment, the distal end of the lead body has a hollow cylindrical tube extending axially and forming a housing for containing the capsule, the helical guide being a helical groove formed in the inner surface of the housing, and means are provided to deploy the capsule anchoring screw by a pin-driven drive.

Preferably, the helix pitch of the helical guide is increased in its free distal end portion. Also preferably, in this embodiment, as in the first embodiment, the capsule has two coupling fingers, one towards the distal end and the other towards the proximal end, and the spacing between the two coupling fingers in the axial direction is selected to provide a compression of the helix when the cylindrical body of the capsule is completely housed inside the helical guide.

In another embodiment, the system of the present invention may further include a flexible wire disposed within and running along a lumen of the lead body having a distal end, connected to the capsule, and a proximal end, extending out the proximal end of the lead body. The flexible wire preferably has in the vicinity of the connection point to the capsule a portion or length made of a resorbable material.

In one embodiment, the capsule can be a capsule for detection/stimulation comprising means for detecting depolarization potentials and/or delivering stimulation pulses and coupled to at least one electrode carried by the capsule, wherein the electrode is an active part of the anchoring screw, and transmitter/receiver wireless communication means for communicating with a remote device.

BRIEF DESCRIPTION OF DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is a perspective view of a first embodiment of a system of a capsule and an implantation accessory in accordance with the present invention in a configuration wherein the two elements are separated;

FIG. 2 shows the system of FIG. 1, in a standalone configuration wherein the capsule is coupled to the implantation accessory before implantation;

FIG. 3 shows the system of FIG. 2, in a configuration during implantation of the capsule in a heart cavity;

FIG. 4 is a perspective sectional view of a second embodiment of an implantation accessory in accordance with the present invention before implantation;

FIG. 5 shows the accessory of FIG. 4, with the capsule housed in the implantation accessory;

FIG. 6 is an enlarged view of the distal portion of the implantation accessory of FIG. 4;

FIG. 7 illustrates a third embodiment of a system of a capsule and an implantation accessory in accordance with the present invention including a flexible wire; and FIGS. 8a and 8b are perspective views, in two different orientations, of the embodiment of FIG. 1 illustrating a reversibility of the implantation of the capsule.

DETAILED DESCRIPTION

Examples of preferred embodiments of the present invention will now be described with reference to the drawings. In FIG. 1, reference 10 designate a capsule having a cylindrical body 12 having an axis and which is provided at one end with a helical anchoring screw 14 axially extending from the tubular body 12 and secured to it in rotation and translation. Anchoring screw 14 preferably includes a distal portion 16 formed along a length of about 1.5 to 2 mm of non-touching turns for penetrating into the cardiac tissue. Distal portion 16 is connected to tubular body 12 via a transition portion 18 having a mechanical bending flexibility, for example, a part formed of contiguous turns in the absence of any stress on the screw.

Anchoring screw 14 may be an electrically active screw. In this regard, at least at its distal end, anchoring screw 14 may serve as a detection and/or stimulation electrode. Alternately, screw 14 may simply be a passive screw only for anchoring the cylindrical body 12 in the wall of the cardiac cavity.

The cylindrical body 12 typically includes various control and power circuits, for signal processing and wireless communication to enable the exchange of signals with a remote device, which may or may not be implanted. These aspects are in themselves known, and as they form no part of the present invention, they will not be described in further detail. One skilled in the art is referred to the various publications cited at the beginning of this description for more details on the structure and function of capsules.

Cylindrical body 12 is cylindrical and preferably includes at least one coupling finger shaped as an axially projecting protuberance, the function of which is explained below. In the examples shown, capsule 10 preferably comprises two such coupling fingers, finger 20 being distally located, and finger 22 being proximally located, with a spacing or gap between fingers 20 and 22 in the axial direction having a predetermined value (the importance of which is explained below). It should be understood that the form of these coupling fingers 20, 22 can be adapted to give them a softened, atraumatic profile.

Cylindrical body 12 typically has a length from about 5 to 10 mm and a diameter from about 1 to 2 mm (i.e., 6 French). Proximal end 24 of capsule 10 can be rounded or domed for, on the one hand, making it atraumatic and, on the other hand, facilitating its coupling with the implantation accessory.

FIGS. 1-3 further illustrate a first embodiment of the implantation accessory 26 used for the implantation of capsule 10.

Accessory 26 generally comprises a body 28 that is structurally similar to a conventional monopolar lead body in that it includes along its entire length, a coiled conductor 30 that is covered by a sheath 32. Sheath 32 is typically made of polyurethane to reduce friction when the lead body is inserted into a guide catheter or the venous system, and to provide better sensitivity and better transmission of torque. In the context of the present invention, however, it should be understood that conductor 30 preferably has no electrical function; rather conductor 30 only contributes to the mechanical behavior of lead body 28 provides radio-opacity to aid in detection of the lead body position, e.g. by fluoroscopy.

The conductor assembly 30/sheath 32 cooperate to provide lead body 28 with a torsional rigidity sufficient to transmit a torque from its proximal end to its distal end to rotate the distal end. It is possible, alternatively or in addition, to introduce in the lumen of lead body 28 a screwing stylet, in particular when the sheath 32 does not present a sufficient torsional stiffness, to rotate directly the distal end of the lead body from the proximal end.

The distal end of lead body 28 is provided with a tip 34 which is secured to a helical guide 36 formed, in this first embodiment, of a number of turns (helix) 38 of an elastic material (e.g., an alloy of the M35N or nitinol type). As a result, helix 38 is compressible in the axial direction, similar to a helical compression spring.

Typically, helix 38 has a reverse pitch compared to the pitch of helical anchoring screw 16 of the capsule, e.g., a left pitch if anchoring screw 16 has a right pitch. In addition, helix 38 has at its free distal end a slightly elongated pitch, for example, on the most distal turn 40.

At the opposite end, helix 38 is connected to tip 34 by a transition portion 42 having a bending flexibility, for example, a portion 42 formed of adjacent turns in the absence of any force acting on helix 38.

During manufacturing, body 12 of capsule 10 is screwed into helix 38, thus resulting in the configuration shown in FIG. 2. The gap between coupling fingers 20 and 22 is sized to ensure, in this configuration, a slight compression of helix 38 when coupling finger 20 engages the distal coil 40 which, as explained above, has an elongated pitch compared to the rest of helix 38.

The entire distal portion is preferably covered with a soluble coating 44, for example, polyethylene glycol (PEG). Soluble coating 44 is provided to protect anchoring screw 14, helix 38 and the surrounding tissue during insertion of the system assembly into and through the venous system. To limit the dissolution time, it is possible to provide the soluble coating with a stepped profile, with the result that the coating around anchoring screw 14 is less thick than elsewhere.

During implantation, the assembly as shown in FIG. 2 is introduced to the cavity using a conventional procedure. Lead body 28 being of a standard construction, the practitioner will find its manipulation will have the classic feel of manipulation of a monopolar lead body with respect to, for example, torque, flexibility and slip.

Once soluble coating 44 is completely dissolved, the physician positions the tip of anchoring screw 14 against the heart wall, and starts screwing, by clockwise rotation (corresponding to a right pitch of the anchoring screw 14). The torque is transmitted from the proximal end of lead body 28 and allows, in a first step, the penetration of the anchoring screw 14 into the tissue of the wall 46 of the cavity of the heart. The corresponding value of torque for this operation is designated as $C_{screwing}$. FIG. 3 shows the configuration of the assembly after complete screwing: the front of capsule 10 abuts against heart wall 46 and thus halts the progression of anchoring screw 14, also generating a significant increase of the reaction torque.

With an anchoring screw of a standard lead, as the practitioner continues rotation of the lead body and of the screw, the torque increases and exceeds a limit $C_{coring}$. Anchoring screw 14 then risks tearing the tissue under the local effect of rotation of the screw without any advance of the screw, causing a laceration to the tissues and, in extreme cases, perforation of the wall with the risk of tamponade.

In contrast, in accordance with the present invention: the physician can pursue without risk the rotation, always clockwise in this embodiment, of lead body 28 because the extra torque occurring due to the reaction of screw 14 anchored in tissue 46 is absorbed by the connection between helix 38 and capsule 10. Specifically, the elasticity in compression of helix 38 is chosen to define a sliding torque $C_{sliding}$ below the limit $C_{coring}$. Thus, when the couple $C_{sliding}$ is reached, further clockwise rotation of lead body 28 starts its rotation around capsule 10, due to the reversed pitch of helix 38. The latter then gradually emerges from capsule 10 by unscrewing (due to the reversal of the pitch). Note that the slightly increased pitch size of last turn 40 can generate a compression of the turns of helix 38 between coupling fingers 20 and 22 (arrows 48), and hence an increasing supporting force of these coupling fingers, until the release of distal finger 20, a situation that defines a release torque $C_{release}$ allowing then the decoupling of capsule 10 and of lead body 28 (arrow 50).

The geometry of the various elements that make this interaction, as well as the elasticity in compression of helix 38, are selected to verify the relationship:

$$C_{screwing} < C_{sliding} < C_{release} < C_{coring}$$

$C_{screwing}$ designating the screwing torque in the tissues, $C_{sliding}$ designating the additional torque absorbed by the connection between the helix and the capsule, $C_{release}$ designating the couple met for the release of the distal finger, and $C_{coring}$ designating the torque limit beyond which the rotation of the anchoring screw may cause a tearing of the tissues of the wall.

It should be understood that the release system, located near anchoring screw 14 and thus at the distal end of the assembly, is not dependent on the torsional behaviour of lead body 28, at the difference, for example, of a system for limiting torque that would be placed proximally.

Moreover, it is noted that during the release, the compressed length helix 38 is maximum, which ensures maximum reproducibility of the release torque.

The mechanism as described above allows absorbing the gradual rise of the torque due to the reaction of the anchoring screw 14 once it is fully inserted in the wall of the heart chamber, with a double benefit of (i) certainty of complete screwing of capsule 10, and (ii) removing of any risk of tamponade.

Advantageously, the whole operation is transparent to the physician, because a single simple rotational movement from the proximal end of lead body 28 ensures both the complete fixation of the capsule and its release.

A second embodiment of the accessory in accordance with the present invention will now be described with reference to FIGS. 4-6. The second embodiment is particularly well suited to embodiments wherein lead body 28 is a standard system known as a pin driven system. A pin driven system is one wherein the practitioner holds in one hand the proximal end of the lead body and in the other hand turns, directly or through a tool, the pin extending from the proximal end. Specifically, the plug is secured to the axial conductor 30 extending within lead body 28, this conductor being then free to rotate relatively to sheath 32 and being connected at its distal end to the tip 34.

In addition, lead body 28 has at its distal end a cylindrical tube 52. Tube 52 has an inner diameter homologous with the outside diameter of capsule 10 (see FIG. 5) and a length allowing it to contain the capsule, including anchoring screw 14, inside the hollow tube.

This second embodiment advantageously does not require use of a soluble PEG coating to protect the screw, because screw 14 can be retracted within tube 52 for the duration of the intravenous transit.

Tube 52 is preferably hollow and provided with a helical groove 54 (seen in particular in the enlarged view of FIG. 6) formed in the inner surface of tube 52 opening into an internal circular recess. Coupling finger 20 thus slides in this helical groove when the connector pin is activated (i.e., employing the pin-driven technique), driving screw 14 out of tube 52.

The helical guide forming a spring is shown at 56. It is in the form of a flat ribbon 56 in an elastically deformable in compression material with a proximal end 58 secured to the tip 34. It has a free distal end 60 which has on its last turn a pitch size slightly increased in the same manner as turn 40 described in the first embodiment.

The direction of the pitch of helical groove 54 is the same as that of anchoring screw 14 (right pitch), however the pitch of flat spring 56 forming a helical guide is a reversed pitch (left pitch).

With this configuration, the rotation of the connector pin at the proximal end of lead body 28 rotates tip 34 and simultaneously capsule 10 and spring 56 in a forward helical movement relative to tube 52. This results in a gradual deployment of screw 14 from tube 52, and then a screwing of screw 14 into wall 46 of the heart cavity, until the front of capsule 10 abuts against wall 46.

The further screwing causes, by the action of helical spring 56 on coupling fingers 20 and 22, the separation of capsule 10 from spring 56, allowing the gradual release of capsule 10 with the same function of disengagement described above with respect to the first embodiment, which prevents tissue damage by the anchoring screw.

Kinematics and stresses on the torque values described in detail for the first embodiment are applicable equally to this second embodiment.

FIG. 7 illustrates a preferred embodiment that can be implemented with either of the first or second embodiments described above, and is designed to allow a repositioning, in the short or in the medium term, of capsule 10 after its initial implantation and release. In this embodiment, separate from the connection between the separable lead body 28 and capsule 10, a flexible wire 62 is connected at its distal end to capsule 10 and passed through the lead body so that its proximal end extends out the proximal end of the lead body (not shown).

Once capsule 10 is implanted, its proper functioning is tested, including if appropriate, the proper establishment of wireless communications between capsule 10 and a remote device (not shown). When capsule 10 is secured, and proper functioning is determined, lead body 28 is completely removed, and an excess length of flexible wire 62 is left to protrude outside the patient, under preferably a protective dressing.

In this regard, flexible wire 62 may be used to retrieve the capsule in case of a displacement in acute phase, by simply pulling on wire 62.

Flexible wire 62 more preferably comprises a region 64 made of a resorbable material at its point of connection with capsule 10, for example, over a length of 3 to 5 mm. This then allows the final withdrawal of flexible wire 62 after a suitable time period, by simply pulling, e.g., one month after surgery.

All or part of the flexible wire 62 may contain an active DSP agent (e.g., Dexamethasone Sodium Phosphate or a like agent to control tissue inflammation (as known to be used in a conventional pacing lead)), or a surface processing intended to stop any spread of infection between the emerging wire part (under the dressing) and the wire part inserted into the venous system.

Further, in the case of a negative functionality test immediately after implantation or in the event of a later malfunction, it is possible to reengage helical guide 36 on the capsule through the guiding of flexible wire 62 and to the rounded shape of rear part 24 of capsule 10. Capsule 10 can then be unscrewed from wall 46 by rotating lead body 28 in a counterclockwise direction and relocated to another site by applying the same system and principle as described above, by namely a clockwise rotation.

Flexible wire 62 can preferably be colored with different colors for each of the implanted capsules in order to more easily identify the relevant capsule (e.g., atrial, ventricular) in the event of an extraction and reimplementation operation.

Advantageously, the present invention thus provides two safety functions for the release of the capsule. The first safety function results from the release system that avoids coring of the heart wall. The second safety function arises by giving the practitioner the opportunity, even after a capsule release, to recover, in the short or medium term, the capsule in case of difficulty, using the flexible wire.

FIGS. 8a and 8b, illustrate according to two different orientations, an alternate embodiment providing reversibility of the implantation of the capsule, in order if necessary to couple again lead body 28 to capsule 10 so as to unscrew it to remove it and possibly relocate it to another site.

Upon replacing the lead body on the capsule, the resetting of helical guide 36 may include to accommodate on capsule 10 in the distal region a compression ramp 66 extending from distal coupling finger 20. Ramp 66 has, as illustrated in FIGS. 8a and 8b, a helical shape 68 extending over the length of a fraction of a turn, with a right pitch (opposite the pitch of helix 38) and having a proximal side 70 against which free end 72 of helix 38 slides. Compression ramp 66 is necessitated by the fact that, in its absence, helix 38, uncompressed when docking with the capsule 10 and then screwing on proximal coupling finger 22, would engage distal coupling finger 20 by its distal end, so that the release mechanism described above would no longer work.

One skilled in the art will understand that the present invention can be practiced by other than the embodiments disclosed herein, which are provided for the purposes of illustration only but not of limitation.

The invention claimed is:

1. A system for implantation of a capsule in a wall of the heart cavity, comprising:
an autonomous capsule having a cylindrical body and at least one coupling finger secured to the cylindrical body and extending radially outward therefrom, wherein the cylindrical body comprises a projecting helical anchoring screw extending axially from one end of the cylindrical body, and wherein the anchoring screw comprises a plurality of coils having a helix direction; and an implantation accessory having a proximal end and a distal end, the implantation accessory comprising a lead body and a helical guide extending axially from the lead body;

wherein the helical guide has an inner diameter that allows the capsule to be positioned within the inner diameter of the helical guide; and wherein the helical guide comprises a plurality of coils having a second helix direction that is opposite to the first helix direction of the anchoring screw.

2. The system of claim 1, wherein the capsule comprises a distal end and a proximal end, a first coupling finger positioned towards the distal end and a second coupling finger positioned towards the proximal end.

3. The system of claim 1, wherein the helical guide is a projecting helix having pitch and axially extending along a length of the distal end of the lead body, and wherein the helix has an axis and is resiliently compressible in an axial direction.

4. The system of claim 3, wherein the pitch of the helix has a free distal end portion and said pitch is increased in the free distal end portion.

5. The system of claim 4, wherein the capsule comprises a distal end and a proximal end, a first coupling finger positioned toward the distal end and a second coupling finger positioned toward the proximal end, the first and second coupling fingers being spaced apart to provide a compression of the helix when the cylindrical body of the capsule is completely housed inside the helical guide.

6. The system of claim 3, wherein when the cylindrical body of the capsule is completely housed inside the helical guide, said system further comprises a soluble protective coating covering the capsule and its anchoring screw within the helical guide.

7. The system of claim 3, wherein the capsule further comprises a reset ramp extending from said at least one coupling finger, said ramp forming a portion of a helical thread with a helix direction opposite to that of the helical guide, and positioned to contact on the proximal side the free end of the helical guide.

8. The system of claim 1, wherein the distal end of the lead body comprises a hollow cylindrical tube extending axially and forming a housing for containing the capsule and having the helical guide, and means for deploying the anchoring screw comprising a pin-driven drive.

9. The system of claim 8, wherein the pitch of the helix has a free distal end portion and said pitch is increased in the free distal end portion.

10. The system of claim 9, wherein the capsule comprises a distal end and a proximal end, a first coupling finger positioned toward the distal end and a second coupling finger positioned toward the proximal end, the first and second coupling fingers being spaced apart to provide a compression of the helix when the cylindrical body of the capsule is completely housed inside the helical guide.

11. The system of claim 1, further comprising a flexible wire disposed in a lumen of the lead body, connecting the capsule to the proximal end of the lead body, said wire comprising near a point of attachment to the capsule a portion made of a resorbable material.

12. An autonomous intracardiac capsule, comprising:

a cylindrical body and at least one coupling finger secured to the cylindrical body and extending radially outward therefrom;

the cylindrical body having an outside diameter and, at a distal end, a projecting helical anchoring screw axially extending from the cylindrical body, to penetrate tissue of the wall of a cavity of the heart, the anchoring screw having a plurality of coils having a helix direction;

the cylindrical body configured to be received by a helical guide on an implantation accessory having a helix direction that is opposite to the helix direction of the anchoring screw, and the at least one coupling finger configured to engage with the helical guide.

13. The capsule of claim 12, further comprising the distal end and a proximal end, a first coupling finger positioned towards the distal end and a second coupling finger positioned towards the proximal end.

14. The capsule of claim 12, further comprising means for detecting depolarization potentials and/or delivering stimulation pulses coupled to at least one electrode carried by the capsule, including an electrode formed by a portion of the anchoring screw, and a transmitter/receiver means for wireless communication with a remote device.

15. The capsule of claim 12, wherein the plurality of coils of the helical anchoring screw further comprises a flexible transition portion and a distal portion of spaced apart coils, wherein the flexible transition portion is between the distal end of the cylindrical body and the spaced apart coils.

16. A method of implanting an autonomous capsule in a tissue wall, comprising:

providing a capsule for implantation by an implantation accessory, wherein the capsule comprises a cylindrical body and at least one coupling finger secured to the cylindrical body and extending radially outward therefrom, wherein the cylindrical body comprises a projecting helical anchoring screw extending axially from one end of the cylindrical body, and wherein the anchoring screw comprises a plurality of coils having a helix direction;

wherein the implantation accessory comprises a lead body and a helical guide having a helix direction opposite of the helix direction of the anchoring screw;

preparing the capsule for implantation by engaging the at least one coupling finger of the capsule with the helical guide and positioning the cylindrical body within the helical guide, wherein the at least one coupling finger is positioned such that as the capsule is engaged with the helical guide the helix is compressed;

introducing the implantation accessory containing the capsule into a cavity of a body;

positioning the anchoring screw at the target tissue wall and engaging the anchoring screw with the target tissue by imparting rotational movement on the lead body;

once the anchoring screw has been engaged with the target tissue and the cylindrical body abuts the target tissue, continuing to impart rotational movement on the lead body, utilizing the opposite helix direction of the anchoring screw and the helical guide, to thereby rotate the helical guide about the cylindrical body to emerge the cylindrical body from the implantation accessory.

17. The method of claim 16, wherein the helical guide is a projecting helix having pitch and axially extending along a length of the distal end of the lead body.

18. The method of claim 16, wherein the distal end of the lead body comprises a hollow cylindrical tube extending axially and forming a housing for containing the capsule and having the helical guide, and means for deploying the anchoring screw comprising a pin-driven drive.

19. The method of claim 16, further comprising covering the anchoring screw and at least a distal portion of the implantation accessory with a soluble coating to protect the surrounding tissue during insertion into the body.

20. The method of claim 16, further comprising:
providing on the capsule a flexible wire extending from the capsule through the lead body of the implantation accessory and being accessible outside of the body.

21. The method of claim 20, further comprising determining whether repositioning of capsule is necessary, and if repositioning is necessary, pulling on the flexible wire to retrieve the capsule.

22. The method of 18, further comprising removing the implantation accessory from the body.

23. The method of claim 20, wherein the flexible wire further comprises a portion comprising resorbable material where the wire connects with the capsule.

* * * * *